(12) United States Patent
Bevinakatti et al.

(10) Patent No.: US 9,695,366 B2
(45) Date of Patent: Jul. 4, 2017

(54) DEMULSIFIERS

(71) Applicant: CRODA INTERNATIONAL PLC, Goole Yorkshire (GB)

(72) Inventors: Hanamanthsa Shankarsa Bevinakatti, Stockton-On-Tees Cleveland (GB); Neil Grainger, Stockton-On-Tees Cleveland (GB); Tracey Joanne Wardell, Stockton-On-Tees Cleveland (GB)

(73) Assignee: Croda International PLC, East Yorkshire (GB)

( * ) Notice: Subject to any disclaimer, the term of this patent is extended or adjusted under 35 U.S.C. 154(b) by 38 days.

(21) Appl. No.: 14/346,083

(22) PCT Filed: Sep. 21, 2012

(86) PCT No.: PCT/GB2012/052340
§ 371 (c)(1),
(2) Date: Mar. 20, 2014

(87) PCT Pub. No.: WO2013/041876
PCT Pub. Date: Mar. 28, 2013

(65) Prior Publication Data
US 2014/0228456 A1 Aug. 14, 2014

(30) Foreign Application Priority Data
Sep. 23, 2011 (GB) .................................. 1116419.1

(51) Int. Cl.
*C10G 33/04* (2006.01)
*B01D 17/04* (2006.01)
*C07C 69/44* (2006.01)
*C11B 13/00* (2006.01)

(52) U.S. Cl.
CPC ........... *C10G 33/04* (2013.01); *B01D 17/047* (2013.01); *C07C 69/44* (2013.01); *C11B 13/00* (2013.01); *Y02W 30/74* (2015.05)

(58) Field of Classification Search
CPC ........ B01D 17/047; C07C 69/44; C10G 33/04
See application file for complete search history.

(56) References Cited

U.S. PATENT DOCUMENTS

| | | | |
|---|---|---|---|
| 4,321,146 A | 3/1982 | McCoy et al. | |
| 4,402,857 A | 9/1983 | Royle | |
| 8,618,180 B2 | 12/2013 | Bruchmann et al. | |
| 2005/0250914 A1* | 11/2005 | Stumbe ................ | C08G 83/005 525/437 |
| 2007/0293634 A1* | 12/2007 | Stumbe ................ | C08G 63/668 525/437 |
| 2008/0153931 A1* | 6/2008 | Bruchmann .......... | B01D 17/047 516/185 |
| 2008/0200544 A1 | 8/2008 | Takeda | |
| 2010/0240857 A1* | 9/2010 | Bruchmann .......... | B01D 17/047 528/272 |

FOREIGN PATENT DOCUMENTS

WO WO 2009/047210 A1 4/2009
WO WO 2010/076253 A1 7/2010

OTHER PUBLICATIONS

Ionescu, M.; Chemistry and Technology of Polyols for Polyurethanes, 2005, p. xiii-xv.*
International Search Report For PCT/GB2012/052340, Issued Jan. 3, 2013.
International Preliminary Report on Patentability and Written Opinion for PCT/GB2012/052340, Mar. 25, 2014.
Bonina et al;"New Oligoethylene Ester Derivative of 5-IDO-2'-Deoxyuridine As Dermal Prodrugs: Synthesis, Physicochemical Properties, and Skin Permeation Studies"; Journal of Pharmaceutical Sciences, vol. 91, No. 1, Jan. 2002, pp. 171-179.

* cited by examiner

Primary Examiner — Robert Jones, Jr.
(74) Attorney, Agent, or Firm — RatnerPrestia

(57) ABSTRACT

The invention relates to novel demulsifiers for use in the demulsification of oils from water and vice versa, including the demulsification of crude oil from sea water or brine. In particular, the present invention relates to novel demulsifiers which are environmentally friendly, or 'green', and which can be used without restriction on-site in offshore oil drilling fields, for example in the North Sea. The novel demulsifiers are based on the reaction product of alkoxylated polyols or polyol esters with dicarboxylic acids.

15 Claims, No Drawings

DEMULSIFIERS

CROSS REFERENCE TO RELATED APPLICATIONS

This application is the U.S. National Phase application of PCT International Application No. PCT/GB2012/052340, filed Sep. 21, 2012, and claims priority of British Patent Application No. 1116419.1, filed Sep. 23, 2011, the disclosures of which are incorporated herein by reference in their entireties for all purposes.

FIELD OF THE INVENTION

The present invention relates to novel demulsifiers for use in the demulsification of oils, including crude oil. In particular, the present invention relates to novel demulsifiers which are environmentally friendly, or 'green', and which can be used without restriction on-site in offshore oil drilling fields, for example in the North Sea. The novel demulsifiers are based on alkoxylated sorbitol or sorbitan esters with dicarboxylic acid.

BACKGROUND OF THE INVENTION

Demulsifiers, or emulsion breakers, are chemicals which are used to separate salted water from crude oil emulsions. They are used in the processing of crude oil which is typically recovered along with significant quantities of brine, usually in the form of sea/ocean water. It is important to remove the brine from the crude oil as quickly as possible to allow dry oil to be stored and shipped as necessary, and to allow 'clean' brine, i.e. brine containing no oil, to be discharged.

Common demulsifiers are generally polymeric surfactants such as copolymers of polyoxyethylene and polypropylene or alkylphenol-formaldehyde resins and/or blends of various surface active substances.

Demulsifiers, like those of the type described above, are contained within the 'clean' brine after demulsification. The easiest and most cost effective way of discharging the 'clean' brine from the crude oil stream is by pumping it back into the sea/ocean onsite. Therefore, the demulsifiers present in the 'clean' brine are also discharged back into the sea/ocean with the brine.

Demulsifiers of the types described above comprise phenol groups, and as such are not environmentally friendly. The discharging of these demulsifiers into the sea increases the levels of phenol groups present in the sea and thus harms marine life present in the area.

In the oilfield industry, there is a move towards more environmentally acceptable chemicals that are less hazardous than the standard production chemicals described above. For example, drilling sites in the North Sea are regulated by the rules of the Convention for the Protection of the Marine Environment of the North-East Atlantic (OSPAR). These rules restrict the toxicity of allowed demulsifiers and place stringent values on the biodegradability and the like of all chemicals to be used in the marine environment. However, it has been generally found that the more environmentally acceptable demulsifiers do not have the same level of efficacy as the standard production chemicals.

There is, therefore, a need for a demulsifier which shows the same or superior properties and efficacy as the standard production chemicals, but which is environmentally friendly and reaches or surpasses the rules of the OSPAR.

It is an object of the present invention to address at least one of the above or other disadvantages associated with the prior art.

SUMMARY OF THE INVENTION

According to a first aspect of the present invention, there is provided a novel demulsifier comprising the reaction product of:
a) an alkoxylated polyol or ester thereof; and
b) a dicarboxylic acid.

According to a second aspect of the present invention, there is provided a novel demulsifier obtainable by reacting:
a) an alkoxylated polyol or ester thereof; and
b) a dicarboxylic acid.

DETAILED DESCRIPTION OF THE PREFERRED EMBODIMENTS

According to at least one embodiment of the present invention, a demulsifier comprises the reaction product of:
a) an alkoxylated polyol or ester thereof; and
b) a dicarboxylic acid.

In accordance with at least one emdodiment, the demulsifier is obtainable by reacting:
a) an alkoxylated polyol or ester thereof; and
b) a dicarboxylic acid.

When used herein, the term "dicarboxylic" refers to an acid comprising two functional groups, i.e. carboxylate groups. The term dicarboxylic acid defines the group of compounds containing both bi-functional carboxylic acids and dimer acids.

The demulsifier is operable to separate oil-in-water and/or water-in-oil emulsions. Preferably, the demulsifier is operable to separate water-in-oil emulsions of the type commonly harvested in crude oil drilling. Preferably, the demulsifier is operable to separate brine from crude oil.

The polyol in the alkoxylated species preferably comprises at least 3 hydroxyl groups. Preferably, the polyol in the alkoxylated species comprises up to 9 hydroxyl groups. Desirably, the polyol has an average of 1 or 2 primary hydroxyl groups and at least 1, preferably 1 to 4 secondary hydroxyl groups.

Preferably, the polyol in the alkoxylated species has the formula (I):

$$R^1\text{—(OH)}_n \quad \text{(I)}$$

where n is from 3 to 8 and particularly from 3 to 6.

The group $R^1$ is desirably an aliphatic hydrocarbyl group. Preferably, the group $R^1$ is saturated. Preferably, $R^1$ has from 3 to 10 carbon atoms, preferably from 3 to 8, and especially from 3 to 6 carbon atoms. $R^1$ will usually be linear, though it may include branching.

Desirably, the polyol in the alkoxylated species has the general formula (Ia):

$$\text{HOH}_2\text{C—(CHOH)}_p\text{—CH}_2\text{OH} \quad \text{(Ia)}$$

where p is from 1 to 6, more preferably from 1 to 4.

Suitable polyols include glycerol, $C_4$ polyols such as threitol and erythritol, $C_5$ polyols such as inositol, arabitol and xylitol and $C_6$ polyols such as sorbitol, and compounds derived therefrom, for example sorbitan. The $C_4$ to $C_6$ polyols are commonly the reduced or hydrogenated forms of corresponding tetrose, pentose and hexose sugars. Desirably the polyol is glycerol or a derivative thereof, particularly sorbitol or sorbitan (usually derived in situ from sorbitol) or a mixture or combination of these.

The polyol may be present in the demulsifier in an esterified form. Preferably, when the polyol is sorbitan, the sorbitan is present in the demulsifier in the form of an ester derived from the reaction of the sorbitan with a fatty acid or derivative thereof. Preferred fatty acids or derivatives thereof comprise in the range from 6 to 24, more preferably 8 to 20, particularly 10 to 18, and especially 12 to 16 carbon atoms. Linear fatty acids are preferred. Suitable fatty acids include capric, lauric, myristic, palmitic, stearic, and/or behenic acid.

Suitable fatty acids or derivatives thereof for reaction with the sorbitol or derivative thereof are preferably derived from natural sources, preferably from vegetable sources. For example, lauric acid is the main acid in coconut oil and in palm kernel oil. It may also be found in animal milk, for example cow's milk and goat's milk. The fatty acids or derivatives thereof may be derived from palm oil, American oil palm oil, nutmeg oil, peach palm seed oil, betel nut, date seed, macadamia nut oil, watermelon seed oil, pumpkin seed or flower oil, and other vegetable sources.

In one embodiment, the polyol or ester thereof is a sorbitan compound, more specifically, a sorbitan ester. Suitable sorbitan esters include sorbitan cocoate, sorbitan caprate, sorbitan laurate, sorbitan myristate, sorbitan palmitate and/or sorbitan stearate. Preferred sorbitan esters are sorbitan caprate and/or sorbitan laurate, preferably sorbitan monolaurate.

The polyol present in the demulsifier is alkoxylated. The alkoxylated polyol preferably comprises residues of an alkoxy group, preferably a univalent radical $R^2$—O—, or anion $R^2$—O$^-$, where $R^2$ is an alkyl group, preferably a $C_1$ to $C_6$ alkyl group, preferably $C_1$ to $C_4$ and more preferably $C_2$ to $C_3$.

Preferably, the alkoxy group is a methoxy group, ethoxy group or propoxy group, preferably ethoxy or propoxy. An increase in the presence of ethoxy groups in the alkoxylated polyol or ester thereof increases the solubility of the demulsifier in water, or in aqueous phases of oil-in-water and/or water-in-oil emulsions. An increase in the presence of propoxy groups in the alkoxylated polyol or ester thereof decreases the solubility of the demulsifier in water, or in aqueous phases of oil-in-water and/or water-in-oil emulsions.

The presence of ethoxy groups in the alkoxylated species increases the hydrophilic-lipophillic balance (HLB) of the alkoxylated species. The presence of propoxy groups in the alkoxylated species lowers the HLB of the alkoxylated species.

Preferably, ethoxy groups are present in the alkoxylated polyol or ester thereof at a pre-determined concentration to provide the desired water solubility and/or HLB in the demulsifier. Alternatively, a mixture of ethoxy and propoxy groups may be present to provide the desired water solubility and/or HLB in the demulsifier.

Preferably, the alkoxylated polyol or ester thereof is derived from the reaction of an alkylene oxide with the polyol or ester thereof. One or more equivalents of alkylene oxide may react with each polyol molecule or molecule of the ester thereof. Preferably, the polyol is polyalkoxylated. Preferably, the alkylene oxide is selected from the group comprising $C_1$ to $C_6$ alkylene oxides, preferably $C_1$ to $C_4$ and more preferably $C_2$ to $C_3$ alkylene oxides. Preferably, the alkylene oxide is ethylene oxide or propylene oxide or a mixture thereof.

Preferably, the alkoxylated polyol or ester thereof comprises between 1 and 500 alkylene oxide equivalents per molecule, preferably between 1 and 400, more preferably between 1 and 200 and most preferably between 2 and 100 alkylene oxide equivalents per molecule.

Where the number of equivalents of alkylene oxide is given in terms of per molecule, preferably, this is the average number of equivalents per molecule in a sample of the product. Individual molecules in the sample may have fewer or greater than the stated number of equivalents of alkylene oxide, but on average, the sample will comprise molecules having an average of the stated number of equivalents of alkylene oxide.

Where the demulsifier comprises an alkoxylated polyol, there are preferably between 1 and 500 alkylene oxide equivalents per molecule, preferably between 2 and 400, more preferably between 5 and 200 and most preferably between 10 and 100 alkylene oxide equivalents per polyol molecule.

Where the demulsifier comprises an alkoxylated ester of a polyol, there are preferably between 1 and 500 alkylene oxide equivalents per molecule, preferably between 2 and 300, more preferably between 3 and 150 and most preferably between 5 and 50 alkylene oxide equivalents per molecule.

In one embodiment, the alkoxylated polyol is preferably an alkoxylated sorbitol, more preferably an ethoxylated sorbitol. Preferably, the alkoxylated polyol comprises between 1 and 500 alkylene oxide equivalents per molecule, preferably between 1 and 400, more preferably between 1 and 200 and most preferably between 2 and 100 alkylene oxide equivalents per sorbitol molecule. Preferably, the alkoxylated sorbitol has the general structure (II):

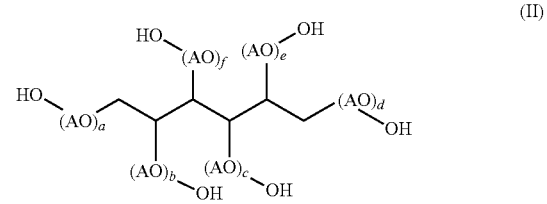

where a,b,c,d,e and f may each independently be any number between 0 and 100; AO is an alkylene oxide residue, preferably an ethylene oxide (EO) residue; and where a+b+c+d+e+f is between 1 and 500, preferably between 1 and 400, more preferably between 1 and 200, even more preferably between 2 and 100 and most preferably between 10 and 40.

Preferably, in this embodiment, the alkoxylated polyol is an ethoxylated sorbitol, more preferably a polyoxyethylene (X) sorbitol, wherein X is a number between 1 and 40, preferably polyoxyethylene (10) sorbitol or polyoxyethylene (40) sorbitol, where a+b+c+d+e+f in formula (II) is 10 or 40, most preferably polyoxyethylene (40) sorbitol, where a+b+c+d+e+f in formula (II) is 40. Polyoxyethylene (40) sorbitol is available commercially from Croda under the trade name Atlas$^{TM}$ G2004.

In another embodiment, the alkoxylated polyol ester is preferably an alkoxylated sorbitan ester, more preferably an ethoxylated sorbitan ester. Preferably, the alkoxylated polyol ester comprises between 1 and 500 alkylene oxide equivalents per molecule, preferably between 1 and 400, more preferably between 1 and 200 and most preferably between 2 and 100 alkylene oxide equivalents per sorbitan ester molecule. Preferably, the alkoxylated sorbitan ester has the general structure (III):

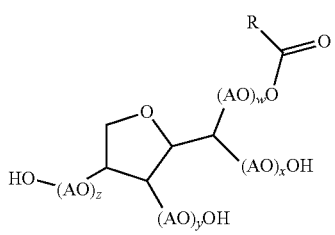

(III)

where w,x,y and z may each independently be any number between 0 and 100; AO is an alkylene oxide residue, preferably an ethylene oxide (EO) residue; R is an alkyl group; and where w+x+y+z is between 1 and 300, preferably between 2 and 200, more preferably between 3 and 100 and most preferably between 5 and 50.

In formula (III), R may be saturated or unsaturated, preferably saturated. R preferably comprises between 1 and 29 carbon atoms, preferably between 5 and 25, preferably between 9 and 21, more preferably between 11 and 17. Preferably R is derived from a fatty acid, preferably selected from the group comprising lauric acid, palmitic acid, stearic acid and oleic acid.

Preferably, in this embodiment, the alkoxylated polyol ester is an ethoxylated sorbitan ester, preferably an ethoxylated sorbitan monolaurate, monopalmitate, monostearate or monooleate, more preferably an ethoxylated sorbitan monolaurate, and most preferably polyoxyethylene (20) sorbitan monolaurate, where w+x+y+z in formula (III) is 20. Polyoxyethylene (20) sorbitan monolaurate is available commercially from Croda under the trade name Tween™ 20.

The dicarboxylic acid present in the demulsifier preferably has from 4 to 40 carbon atoms. Preferably, the dicarboxylic acid is aliphatic. Typically, the dicarboxylic acid is of the formula (IV):

HOOC—R³—COOH    (IV)

where $R^3$ is a $C_2$ to $C_{36}$ hydrocarbyl group which can be saturated or unsaturated, linear or branched and can be aromatic e.g. a phenyl ring (thus giving a phthalic, terephthalic or iso-phthalic dicarboxylic acid) or, desirably, aliphatic e.g. an alkylene or alkenylene group, and may be cyclic though it is desirably open chain. Commonly $R^3$ R is a group: —$(CH_2)_m$-, where m is from 2 to 36. Suitable reactive derivatives of the dicarboxylic acids include lower e.g. $C_1$ to $C_4$ and particularly methyl, alkyl esters (usually diesters) and anhydrides, particularly cyclic anhydrides such as succinic, maleic and phthalic anhydrides.

In one embodiment, the dicarboxylic acid has at least 4 carbon atoms, preferably at least 5 and more preferably at least 6 carbon atoms. In this embodiment, the dicarboxylic acid preferably comprises up to 36 carbon atoms, preferably up to 20 carbon atoms, more preferably up to 12 carbon atoms and most preferably up to 10 carbon atoms. In this embodiment, the dicarboxylic acid may be selected from the group comprising malonic acid, succinic acid, glutaric acid, adipic acid, pimelic acid, suberic acid, axelaic acid and sebacic acid, preferably adipic acid, suberic acid and sebacic acid, more preferably adipic acid.

In another embodiment, the dicarboxylic acid is preferably a dimer acid. In this embodiment, the dimer acid preferably comprises from 24 to 52 carbon atoms, preferably from 28 to 48 carbon atoms, more preferably from 32 to 46 carbon atoms and most preferably from 36 to 44 carbon atoms. Preferably the dimer acid is a C36 dimer acid.

The term dimer fatty acid is well known in the art and refers to the dimerisation product of mono- or polyunsaturated fatty acids and/or esters thereof. Preferred dimer acids are dimers of $C_{10}$ to $C_{30}$, more preferably $C_{12}$ to $C_{24}$, particularly $C_u$ to $C_{22}$, and especially $C_{18}$ alkyl chains. Suitable dimer fatty acids include the dimerisation products of oleic acid, linoleic acid, linolenic acid, palmitoleic acid, and elaidic acid. The dimerisation products of the unsaturated fatty acid mixtures obtained in the hydrolysis of natural fats and oils, e.g. sunflower oil, soybean oil, olive oil, rapeseed oil, cottonseed oil and tall oil, may also be used. Hydrogenated, for example by using a nickel catalyst, dimer fatty acids may also be employed.

In addition to the dimer fatty acids, dimerisation usually results in varying amounts of oligomeric fatty acids (so-called "trimer") and residues of monomeric fatty acids (so-called "monomer"), or esters thereof, being present. The amount of monomer can, for example, be reduced by distillation. Particularly preferred dimer fatty acids have a dicarboxylic (or dimer) content of greater than 70%, more preferably greater than 85%, and particularly greater than 94% by weight.

Preferably, the molar ratio of alkoxylated polyol or ester thereof to dicarboxylic acid in the reaction product is at least 0.05:1, preferably at least 0.1:1, more preferably at least 0.5:1 and most preferably at least 1:1. Preferably, the molar ratio of alkoxylated polyol or ester thereof to dicarboxylic acid in the reaction product is up to 20:1, preferably up to 10:1, more preferably up to 5:1 and most preferably up to 3:1.

Optionally, the reaction product of the alkoxylated polyol or ester thereof and the dicarboxylic acid may further comprise an end-cap. Preferably, the end-cap comprises a monovalent radical. Preferably, the end-cap comprises a monocarboxylic acid.

Preferably, the monocarboxylic acid is a fatty acid. Preferably, the monocarboxylic acid comprises from 2 to 30 carbon atoms preferably between 12 and 26, more preferably between 14 and 22 carbon atoms and most preferably between 18 and 22 carbon atoms. The monocarboxylic acid may be selected from the group comprising lauric acid, myristic acid, palmitic acid, stearic acid, arachidic acid and behenic acid, preferably stearic acid and behenic acid.

Fatty acids suitable for use herein can be obtained from natural sources such as, for example plant or animal esters. For example, the acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures employed. Resin acids, such as those present in tall oil, may also be used.

Preferably, the monocarboxylic acid is saturated. The fatty acid may be either a branched fatty acid or a linear fatty acid. A mixture of fatty acids may be present. In this case, the mixture may comprise branched fatty acids, linear fatty acids, or a mixture thereof.

Preferably, the molar ratio of the end-cap to the reaction product of the alkoxylated polyol or ester thereof and the dicarboxylic acid is at least 0.05:1, preferably at least 0.1:1, more preferably at least 0.2:1 and most preferably at least 0.35:1. Preferably, molar ratio of the end-cap to the reaction product of the alkoxylated polyol or ester thereof and the dicarboxylic acid is up to 20:1, preferably up to 10:1, more preferably up to 5:1 and most preferably up to 2:1.

Preferably, the molar ratio of the alkoxylated polyol or ester thereof to the dicarboxylic acid to the end-cap is at least 1:0.1:1 and more preferably at least 1:0.5:1. Preferably, molar ratio of the end-cap to the reaction product of the alkoxylated polyol or ester thereof and the dicarboxylic acid is up to 1:1:5 and more preferably up to 1:1:2.

Preferably, the reaction product has a molecular weight of greater than 700 Daltons, preferably greater than 1000 Daltons, more preferably greater than 1500 Daltons and most preferably greater than 2000 Daltons. Preferably, the reaction product has a molecular weight of less than 100000 Daltons, preferably less than 80000 Daltons, more preferably less than 50000 Daltons and most preferably less than 20000 Daltons.

Preferably, the reaction product has a relative solubility number (RSN) of at least 2, preferably at least 4, more preferably at least 6 and most preferably at least 8. Preferably, the reaction product has an RSN of up to 100, preferably up to 60, more preferably up to 30 and most preferably up to 20. The RSN is a measure of the solubility of the demulsifier and corresponds to the hydrophilic-lipophilic balance of the demulsifier. The RSN can be determined according to the method set out in Wu et al, Colloids and surfaces: A, Physicochemical and engineering aspects; 2004; Vol. 232(2-3); pages 229-237.

Preferably, the reaction product has a toxicity of less than 20,000mg/l, preferably less than 15,000 mg/l, preferably less than 10,000 mg/l and most preferably less than 5,500mg/l. The toxicity is determined according to the method set out below in Experimental Example 2.

Preferably, the reaction product shows a biodegradation of at least 1%, preferably at least 5%, more preferably at least 8% and most preferably at least 10%. The biodegradation is determined according to the method set out below in Experimental Example 2

Preferably, the reaction product has a viscosity at 25° C. of greater than 100 mPa·s, preferably greater than 300 mPa·s, more preferably greater than 500 mPa·s and most preferably greater than 900 mPa·s. The viscosity is measured at 25° C. on a Brookfield viscometer using a 29 Spindle at a shear rate of 0.25N.

Preferably, the reaction product has a pour point of less than 100° C., preferably less than 80° C., more preferably less than 50° C. and most preferably less than 30° C.

Preferably, the reaction product has a pour point of greater than 1° C., preferably greater than 5° C., more preferably greater than 10° C. Preferably, the pour point is measured on an ISL MPP 5Gs automated pour point analyser according to the ASTM D97 standard method.

Preferably, the reaction product has a pH which is approximately neutral. Preferably, the reaction product has a pH of between 3 and 12, preferably between 4 and 10, more preferably between 5 and 8 and most preferably between 6 and 7. The pH of the reaction product is measured at a concentration of 1% in an 85% IPA solution using an HI 8424 portable pH probe.

Preferably, the reaction product has a density at 25° C. of at least 0.1 g/cm$^3$, preferably at least 0.5 g/cm$^3$, more preferably at least 0.8 g/cm$^3$, and most preferably at least 1.0 g/cm$^3$. Preferably, the reaction product has a density at 25° C. of up to 10 g/cm$^3$, preferably up to 5 g/cm$^3$, more preferably up to 3 g/cm$^3$, and most preferably up to 2 g/cm$^3$.

The density may be determined by pouring 10 ml of sample into a measuring cylinder and calculating the approximate density from the weight.

Preferably, the reaction product has good thermal stability in air and/or nitrogen. Preferably, the reaction product is stable in air up to a temperature of at least 50° C., preferably at least 100° C., more preferably at least 150° C. and most preferably at least 200° C. before the product starts to degrade. Preferably, the reaction product is stable in nitrogen up to a temperature of at least 50° C., preferably at least 100° C., more preferably at least 150° C. and most preferably at least 200° C. before the product starts to degrade. The thermal stability in air and nitrogen was measured according to the method set out in Experimental Example 1 below.

Preferably, the reaction product shows a mass loss in air over a period of 1 hour at 150° C. of less than 50%, preferably less than 30%, more preferably less than 15% and most preferably of less than 7%. Preferably, the reaction product shows a mass loss in air over a period of 1 hour at 200° C. of less than 90%, preferably less than 85%, more preferably less than 80% and most preferably of less than 75%. The mass loss was measured according to the method set out in Experimental Example 1 below.

Preferably, the demulsifier is used at a dosage rate of between 0.01 and 1000 ppm, preferably between 0.05 and 800 ppm, more preferably between 0.1 and 500 ppm and most preferably between 0.5 and 100 ppm in the emulsion to be demulsified.

It should be noted that particular demulsifiers can be extremely emulsion-specific. Therefore, the failure of a demulsifier to work on one or two tests does not mean that the demulsifier is unsuitable everywhere. This fact makes it extremely difficult to judge the worth of a particular potential demulsifier based on a few negative results alone. Positive results, however, may point to the worth not only of the demulsifier itself, but of the class of chemistry that that particular demulsifier represents. Consequently, the existence of several cases of outstanding positive performance gives credibility to this invention as a whole.

According to a second aspect of the present invention, there is provided a demulsification formulation comprising a demulsifier which is the reaction product of:
  a) an alkoxylated sorbitol or sorbitan ester;
  b) a dicarboxylic acid; and
  c) optionally, an end-cap.

Preferably, the demulsification formulation is for demulsifying an oil-in-water or a water-in-oil emulsion.

Preferably, the demulsifier which is the reaction product of the alkoxylated polyol or ester thereof, dicarboxylic acid and optional end-cap is present in the demulsification formulation at a concentration of at least 2% w/w based on the total weight of the demulsification formulation, preferably at least 5% w/w, more preferably at least 10% w/w and most preferably at least 15% w/w. Preferably, the demulsifier is present in the demulsification formulation at a concentration of up to 80% w/w based on the total weight of the demulsification formulation, preferably up to 60% w/w, more preferably up to 50% w/w and most preferably up to 30% w/w.

Preferably, the demulsification formulation also comprises a solvent. The solvent is preferably a derivative of the oil phase of the emulsion to be demulsified. For example, for crude oil, the solvent may be selected from xylene, heavy or light aromatic naphtha, IPA, methanol 2EH, diesel or toluene.

Preferably, the solvent is present in the demulsification formulation at a concentration of at least 20% w/w based on the total weight of the demulsification formulation, preferably at least 30% w/w, more preferably at least 40% w/w and most preferably at least 50% w/w. Preferably, the solvent is present in the demulsification formulation at a concentration of up to 98% w/w based on the total weight of the demulsification formulation, preferably up to 90% w/w, more preferably up to 80% w/w and most preferably up to 70% w/w.

Preferably, the solvent is present in the demulsification formulation at a ratio to the demulsifier of up to 50:1, preferably up to 30:1, more preferably up to 20:1 and most preferably up to 10:1. Preferably, the solvent is present in the demulsification formulation at a ratio to the demulsifier of at least 1:10, preferably at least 1:5, more preferably at least 1:2 and most preferably at least 1:1.

The demulsification formulation may optionally further comprise a wetting agent. Preferably, the wetting agent is a surfactant, preferably an anionic surfactant. Preferably, the wetting agent is or comprises an ester. Any suitable surfactant, particularly an ester-containing surfactant, or mixtures thereof may be used as the wetting agent in the present invention. Examples of suitable wetting agents include, but are not limited to alkyl sulfates, such as ammonium lauryl sulfate, sodium lauryl sulfate; alkyl ether sulfates, such as sodium laureth sulfate, also known as sodium lauryl ether sulfate (SLES), sodium myreth sulfate; sulfonates such as dioctyl sodium sulfosuccinate, perfluorooctanesulfonate (PFOS), perfluorobutanesulfonate; alkyl benzene sulfonates; phosphates such as alkyl aryl ether phosphate, akyl ether phosphate, carboxylates such as alkyl carboxylates, i.e. Fatty acid salts (soaps), sodium stearate, Sodium lauroyl sarcosinate, carboxylate fluorosurfactants (perfluorononanoate, perfluorooctanoate (PFOA or PFO)) and Synperonic™ LF/30 (ex Croda).

When present, the wetting agent is preferably present in the demulsification formulation at a concentration of at least 1% w/w based on the total weight of the demulsification formulation, preferably at least 3% w/w, more preferably at least 6% w/w and most preferably at least 8% w/w. Preferably, when present, the wetting agent is present in the demulsification formulation at a concentration of up to 25% w/w based on the total weight of the demulsification formulation, preferably up to 20% w/w, more preferably up to 15% w/w and most preferably up to 12% w/w.

The demulsification formulation may optionally further comprise an alkylene oxide block copolymer, for example an ethylene oxide (EO)/propylene oxide (PO) block copolymer. The block copolymer may be either an EO-P0 copolymer, EO-PO-EO copolymer or PO-EO-PO copolymer. Preferably, the block copolymer has a molecular weight of between approximately 1000 and 10000, preferably between 1500 and 8000, more preferably between 2000 and 7000. Preferably, the block copolymer has an HLB of between 0.1 and 20, preferably between 0.5 and 17, and ore preferably between 1 and 15. Examples of suitable block copolymers include, but are not limited to Surfonic™ EO/PO block copolymers ex Huntsman and EO/PO block copolymers from Ineos Oxide.

When present, the alkylene oxide block copolymer is preferably present in the demulsification formulation at a concentration of at least 1% w/w based on the total weight of the demulsification formulation, preferably at least 3% w/w, more preferably at least 6% w/w and most preferably at least 8% w/w. Preferably, when present, the alkylene oxide block copolymer is present in the demulsification formulation at a concentration of up to 25% w/w based on the total weight of the demulsification formulation, preferably up to 20% w/w, more preferably up to 15% w/w and most preferably up to 12% w/w.

Preferably, the demulsification formulation is anhydrous. Preferably, the demulsification formulation comprises less than 5% water, preferably less than 3%, more preferably less than 2% and most preferably less than 1% water.

It will be appreciated that the exact composition of demulsifying formulations will vary according to the particular emulsion it is to be used on, and even for crude oil obtained from the same well, over time, the optimum amount of demulsifier will vary as the production conditions change. For example, different temperature and pressure conditions, concentrations of naturally occurring emulsifiers, production techniques, etc., make it impossible to predict in advance the demulsifier proportions required.

Preferably, the demulsification formulation is used at a dosage rate of between 1 and 1000 ppm, preferably between 5 and 800 ppm, more preferably between 15 and 500 ppm and most preferably between 20 and 200 ppm in the emulsion to be demulsified.

According to a third aspect of the present invention, there is provided a method of demulsifying an oil-in-water or water-in-oil emulsion, the method comprising adding a reaction product of:
  a) an alkoxylated sorbitol or sorbitan ester;
  b) a dicarboxylic acid; and
  c) optionally, an end-cap to the emulsion.

Preferably, the emulsion is a water-in-oil emulsion. Preferably, the emulsion is an emulsion of water, preferably salted water, more preferably sea/ocean water in crude oil.

According to a further aspect of the invention, there is provided the use of a reaction product of:
  a) an alkoxylated sorbitol or sorbitan ester;
  b) a dicarboxylic acid; and
  c) optionally, an end-cap
as a demulsifier.

Preferably, the reaction product is used in the demulsification of an oil-in-water or water-in-oil emulsion, preferably a crude oil emulsion.

Any of the above features of the invention may be combined in any combination and with any aspect of the invention.

EXAMPLES

The present invention will now be described further, for illustrative purposes only, in the following examples. All parts and percentages are given by weight unless otherwise stated.

Preparation Process

Demulsifier 1

A composition comprising sorbitan (20EO) monolaurate and adipic acid in a 2:1 molar ratio was produced.

384 kg of sorbitan (20EO) monolaurate was added to the reaction vessel and heated to 80° C. whilst stirring. 23 kg of adipic acid flake was slowly added to the warm stirred sorbitan (20EO) monolaurate. The mixture was heated to 235° C. observing distillation water removal. The reaction was continued until an acid value of the less than 5 mgKOH/g was observed.

The reaction yielded 400 kg of reaction product and 5.8 kg water.

Demulsifier 2

A composition comprising sorbitan (20EO) monolaurate, adipic acid and stearic acid in a 2:1:2 molar ratio was produced.

313 kg of sorbitan (20EO) monolaurate was added to the reaction vessel and heated to 60° C. whilst stirring. 73 kg of stearic acid flake was slowly added to the warm stirred sorbitan (20EO) monolaurate and the resulting mixture heated to 80° C. 19 kg of adipic acid flake was then added to the mixture in the reaction vessel. The mixture was heated to 235° C. observing distillation water removal. The reaction was continued until an acid value of the less than 5 mgKOH/g was observed.

The reaction yielded 400 kg of reaction product and 4.8 kg water.

Demulsifier 3

A composition comprising sorbitol (40EO), adipic acid and stearic acid in a 1:1:2 molar ratio was produced.

299 kg of sorbitol (40EO) was added to the reaction vessel and heated to 60° C. whilst stirring. 86 kg of stearic acid flake was slowly added to the warm stirred sorbitol (40EO) and the resulting mixture heated to 80° C. 23 kg of adipic acid flake was then added to the mixture in the reaction vessel. The mixture was heated to 235° C. observing distillation water removal. The reaction was continued until an acid value of the less than 5mgKOH/g was observed.

The reaction yielded 400 kg of reaction product and 8.3 kg water.

Demulsifier 4

A composition comprising sorbitol (40EO) and $C_{36}$ dimer acid in a 4:3 molar ratio was produced.

72 kg of $C_{36}$ dimer acid was added to the reaction vessel and heated to 80° C. whilst stirring. 335 kg of sorbitol (40EO) was slowly added to the warm stirred $C_{36}$ dimer acid. The mixture was heated to 235° C. observing distillation water removal. The reaction was continued until an acid value of the less than 5mgKOH/g was observed The reaction yielded 400 kg of reaction product and 5 kg water.

Formulation 1

A formulation was prepared comprising the following:

| | |
|---|---|
| Demulsifier 1 | 20% |
| EO/PO block polymer (Surfonic ™ block copolymer, ex Huntsman) | 10% |
| Ester/wetting agent (ethylene oxide/propylene oxide copolymer, based on a C13/C15 alcohol, for example Synperonic ™ LF/30, ex Croda) | 10% |
| Solvent (diesel) | 60% |

Formulation 2

A formulation was prepared comprising the following:

| | |
|---|---|
| Demulsifier 3 | 30% |
| EO/PO block polymer (Surfonic ™ block copolymer, ex Huntsman) | 12% |
| Ester/wetting agent (ethylene oxide/propylene oxide copolymer, based on a C13/C15 alcohol, for example Synperonic ™ LF/30, ex Croda) | 8% |
| Solvent (methanol) | 50% |

Experimental

Physical Properties and Thermal Stability

A) The physical properties of the demulsifiers 1-4 were tested. The results and standard testing methods are detailed in Table 1 below.

TABLE 1

| | | Physical properties | | | | | | |
|---|---|---|---|---|---|---|---|---|
| Demulsifier | Appearance | Viscosity 25° C. mPa · s (cP) Brookfield Spindle 29 | Density 25° C. (g/cm³) Using a measuring cylinder | Cloud Point ° C. 5% sample in 35% BDG: 65% DI Water | Pour Point ° C. Pour Point Analyser | Solubility 1% Sample in DI Water | pH 1% Sample in 85:15 IPA:DI Water | Relative Solubility Number (RSN) |
| 1 | Pale waxy solid | 970 | 1.0552 | +82 | +24 | Insoluble | 6.1 | 16 |
| 2 | Amber liquid | 1330 | 1.092 | +60 | −9.0 | Soluble | 7.0 | 17 |
| 3 | Opaque amber liquid | 1140 | 1.0853 | Cloudy | +18.0 | Insoluble | 7.2 | 9 |
| 4 | Yellow clear liquid | 2260 | 1.0349 | >90 | −3.0 | Soluble | 6.9 | 19 |

B) The thermal stability of the demulsifiers was then tested in air. The tests were performed at 150° C. and 200° C. The experimental method was as follows.

Thermogravimetric Analysis (TGA) at 150° C. over 1 hour

Between 10 and 15 mg of the sample to be tested was weighed into a

70 μL alumina crucible put into the thermogravimetric analyser's (Mettler TG50) furnace and run under air at the following conditions:

Gas (flow rate): Air (200 ml/min)

Temperature range:

30-150° C. at 50° C./min then

150° C. for one hour then 150-600° C. at 50° C./min then

600° C. for five minutes.

TGA Analysis at 200° C. over 1 hour

The method as described above was performed, but over the below temperature range:

30-200° C. at 50° C./min then

200° C. for one hour then 200-600° C. at 50° C./min then

600° C. for five minutes.

The percentage mass lost was calculated by step horizontal analysis using STARe software (version 9.2) on the results of the two methods described above. The results are shown in Table 2 below.

TABLE 2

Mass loss results

| Demulsifier | Mass lost at 150° C. (%) | Mass lost at 200° C. (%) |
|---|---|---|
| 1 | 6.6 | 55.7 |
| 2 | 4.5 | 70.1 |
| 3 | 2.7 | 50.5 |
| 4 | 2.9 | 43.6 |

Toxicity and Biodegradation

The biodegradation of the demulsifiers was tested according to the guidelines set out in OECD 306 "Biodegradability in Sea Water" (Adopted: 17.07.92). The method set out on pages 10 to 17 of the guidelines, i.e. the closed bottle method, was performed. The results are given in Table 3 below.

The toxicity of the demulsifiers was tested according to ISO 10253 (Second edition, 15.04.2006). The results are given in Table 3 below.

TABLE 3

Toxicity and Biodegradation Results

| Demulsifier | Toxicity (mg/l) | Biodegradation (%) |
|---|---|---|
| 1 | 238 | 32 |
| 2 | 47 | 43 |
| 3 | 648 | 47 |
| 4 | 5008 | 11 |

From the results it can be seen that all of the demulsifiers have low toxicity and good biodegradation properties.

Efficacy Tests

Samples of crude oil used was classified using the American Petroleum Institute (API) test guidelines. The oil was obtained from a UK onshore source at Star Energy located near to Lincoln in April 2011. The crude oil samples were cut with water at the percentages described below in Table 4.

TABLE 4

Crude Oil Water Cut

| Water Cut (%) | API (°) | Crude Oil Type |
|---|---|---|
| 10 | 14.4 | Heavy |
| 30 | 15.9 | Heavy |
| 50 | 11.4 | Heavy |
| 70 | 11.4 | Heavy |

Tests were performed on the oil samples from Table 4 to determine the effectiveness of the Demulsifiers described above. The tests were carried out using a TurbiScan TLab Thermo manufactured by Formulaction. The demulsifiers were added to the crude oil at a concentration of 100 ppm (in xylene) and analysed in the TurbiScan at 1 scan per minute for 60 minutes. The temperature of the TurbiScan was 60° C.

The TurbiScan monitors the duration of the demulsification, along with the transmission level and clarity of the resulting water phase and the quality of the interface between the resulting water and oil phases.

The results of the TurbiScan tests are given in Table 5.

TABLE 5

TurbiScan test results

| Demulsifier | Crude Oil Water Cut (%) | Time Demulsification Started (minutes) | Time Demulsification finished (minutes) | Water Out (%) | Transmission Level (%) | Water Clarity | Interface Quality |
|---|---|---|---|---|---|---|---|
| 1 | 10 | 8 | 30 | 55 | >80 | Very clear | Excellent |
| 1 | 30 | 34 | >60 | 55 | >80 | Very clear | Excellent |
| 1 | 50 | 32 | 55 | 55 | >80 | Very clear | Excellent |
| 1 | 70 | 4 | 12 | 68 | >60 | Average | Excellent |
| 2 | 10 | 10 | 50 | 52 | >80 | Very clear | Excellent |
| 2 | 30 | 31 | >60 | 40 | >80 | Very clear | Excellent |
| 2 | 50 | 29 | 50 | 49 | >80 | Very clear | Excellent |
| 2 | 70 | 6 | 50 | 66 | >70 | Clear | Excellent |
| 3 | 10 | 8 | 20 | 56 | ≈40 | Poor | Average |
| 3 | 30 | 8 | 20 | 59 | ≈50 | Average/Poor | Average |
| 3 | 50 | 8 | 35 | 56 | ≈60 | Average | Average |
| 3 | 70 | 2 | 50 | 62 | ≈30 | Poor/cloudy | Average |
| 4 | 10 | 6 | >60 | 33 | >80 | Very clear | Excellent |
| 4 | 30 | 44 | >60 | 7 | >80 | Very clear | Excellent |
| 4 | 50 | 29 | >60 | 31 | >80 | Very clear | Excellent |
| 4 | 70 | 3 | 55 | 58 | >70 | Clear | Excellent |

The present invention, therefore, provides a demulsifier which shows the same or superior properties and efficacy as the standard production chemicals, but which is environmentally friendly and reaches or surpasses the rules of the OSPAR.

The demulsifier of the present invention shows good stability, so it can easily be stored onsite at off-shore drilling locations until required for use. When used, the demulsifier shows good efficacy in demulsifying crude oil emulsions, and has superior biodegradability and toxicity properties meaning it can safely be discharged into the sea/ocean without further treatment of the aqueous phase of the demulsified emulsion being required.

Any or all of the disclosed features, and/or any or all of the steps of any method or process described, may be combined in any combination.

Each feature disclosed herein may be replaced by alternative features serving the same, equivalent or similar purpose. Therefore, each feature disclosed is one example only of a generic series of equivalent or similar features.

The above statements apply unless expressly stated otherwise. The term specification, for these purposes, includes the description and any accompanying claims, abstract and drawings.

The invention claimed is:

1. A demulsifier comprising the reaction product of:
   a) an alkoxylated sorbitan or ester thereof; and
   b) a dicarboxylic acid, wherein the dicarboxylic acid is selected from the group consisting of malonic acid, glutaric acid, adipic acid, pimelic acid, suberic acid, azelaic acid, sebacic acid, and dimer acid.

2. The demulsifier according to claim 1, wherein the demulsifier is operable to separate oil-in-water and/or water-in-oil emulsions.

3. The demulsifier according to claim 1, wherein the alkoxylated sorbitan or ester thereof comprises between 1 and 500 alkylene oxide equivalents per molecule.

4. The demulsifier according to claim 1, wherein the molar ratio of alkoxylated sorbitan or ester thereof to dicarboxylic acid in the reaction product is at least 0.05:1 and up to 20:1.

5. The demulsifier according to claim 1, wherein the reaction product of the alkoxylated sorbitan or ester thereof and the dicarboxylic acid further comprises an end-cap.

6. The demulsifier according to claim 5, wherein the end-cap comprises a monocarboxylic acid.

7. The demulsifier according to claim 5, wherein the molar ratio of the end-cap to the reaction product of the alkoxylated sorbitan or ester thereof and the dicarboxylic acid is at least 0.05:1 and up to 20:1.

8. The demulsifier according to claim 5, wherein the molar ratio of the alkoxylated sorbitan or ester thereof to the dicarboxylic acid to the end-cap is at least 1:0.1:1 and up to 1:1:5.

9. A demulsification formulation comprising a demulsifier which is the reaction product of:
   a) an alkoxylated sorbitan ester;
   b) a dicarboxylic acid, wherein the dicarboxylic acid is selected from the group consisting of malonic acid, glutaric acid, adipic acid, pimelic acid, suberic acid, azelaic acid, sebacic acid, and dimer acid; and
   c) optionally, an end-cap.

10. A method of demulsifying an oil-in-water or water-in-oil emulsion, the method comprising adding a reaction product of:
    a) an alkoxylated sorbitan ester;
    b) a dicarboxylic acid, wherein the dicarboxylic acid is selected from the group consisting of malonic acid, glutaric acid, adipic acid, pimelic acid, suberic acid, azelaic acid, sebacic acid, and dimer acid; and
    c) optionally, an end-cap to the emulsion.

11. A method for obtaining a demulsifier, comprising reacting:
    a) an alkoxylated sorbitan or ester thereof; with
    b) a dicarboxylic acid, wherein the dicarboxylic acid is selected from the group consisting of malonic acid, glutaric acid, adipic acid, pimelic acid, suberic acid, azelaic acid, sebacic acid, and dimer acid.

12. A demulsifier comprising the reaction product of:
    a) an alkoxylated sorbitol or sorbitan or ester thereof; and
    b) a dicarboxylic acid, wherein the dicarboxylic acid is selected from the group consisting of malonic acid, glutaric acid, adipic acid, pimelic acid, suberic acid, azelaic acid, sebacic acid, and dimer acid; and
    c) an end-cap selected from the group consisting of lauric acid, myristic acid, palmitic acid, stearic acid, arachidic acid, and behenic acid;
    wherein the molar ratio of the alkoxylated sorbitol or sorbitan or ester thereof to the dicarboxylic acid to the end-cap is at least 1:0.1:1 and up to 1:1:5.

13. The demulsifier according to claim 12, wherein the molar ratio of the alkoxylated sorbitol or sorbitan or ester thereof to the dicarboxylic acid to the end-cap is up to 1:1:2.

14. The demulsifier according to claim 12, wherein the molar ratio of the alkoxylated sorbitol or sorbitan or ester thereof to the dicarboxylic acid to the end-cap is at least 1:0.5:1.

15. The demulsifier according to claim 12, wherein the alkoxylated sorbitol or sorbitan or ester thereof comprises between 1 and 500 alkylene oxide equivalents per molecule.

* * * * *